United States Patent [19]

Bisso et al.

[11] Patent Number: 4,925,801
[45] Date of Patent: May 15, 1990

[54] PROCESS FOR PRESERVING THE PHOSPHORYLATING ACTIVITY OF YEAST, APPLIED TO THE PRODUCTION OF FRUCTOSE-1,6-DIPHOSPHATE

[76] Inventors: Guillermo Bisso, Via A.G. Barriti; Federico Melelli, Via Domodossola 26, both of Rome, Italy

[21] Appl. No.: 29,335

[22] Filed: Mar. 23, 1987

[30] Foreign Application Priority Data

Mar. 25, 1986 [IT] Italy ............................. 19865 A/86

[51] Int. Cl.$^5$ ...................... C12N 15/00; C12N 5/00; C12N 7/00
[52] U.S. Cl. ................................. 435/255; 435/135; 435/174; 435/175; 435/188; 435/320; 435/317.1; 435/941; 435/942; 530/810
[58] Field of Search ............... 435/105, 174, 175, 188, 435/317.1, 255, 941, 942; 530/810

[56] References Cited

U.S. PATENT DOCUMENTS

| | | | |
|---|---|---|---|
| 3,950,222 | 4/1976 | Takasaki | 195/68 |
| 4,288,552 | 9/1981 | Gestrelius | 435/174 |
| 4,575,549 | 3/1986 | Diana | 536/117 |
| 4,600,692 | 7/1986 | Wood et al. | 435/108 |

OTHER PUBLICATIONS

Wemberg, R.; Elution of Low Molecular Weight Solutes from Viable Cells of *Saccharomycei bisporus*; Arch Microbial 134 (4), pp. 329-334 (1983).

Ruby, S. W. et al.; Clonids Regulated Yeast Genes from a Pool of Lac Z Fusions; Methods in Enz 101, pp. 253-269 (1983).

Fraenkel, D. G.; Carbohydrate Metabolism; from the *Molecular Biology of the Yeast Saccharomyces;* Cold Spring Harbor Press; N.Y. (1982), eds. Strathern et al., pp. 1-13.

Metzler, D. E.; *Biochemistry;* Academic Press (1977), pp. 119, 638-640.

Primary Examiner—Robin L. Teskin
Attorney, Agent, or Firm—Ladas & Parry

[57] ABSTRACT

A process for preserving the phosphorylating activity of brewer's yeast by means of the intracellular immobilization of the glycolytic enzymes by glutaraldehyde. The process provides the following steps:
  permeabilization of the cell wall by the combined effect of temperature and the osmotic shock caused by the addition of a concentrated solution of dextrose and phosphates;
  immobilization of the glycolytic enzymes by crosslinking with intracellular proteins;
  protection of the SH groups against possible oxidation by the addition of deproteinized yeast extract.

6 Claims, No Drawings

PROCESS FOR PRESERVING THE PHOSPHORYLATING ACTIVITY OF YEAST, APPLIED TO THE PRODUCTION OF FRUCTOSE-1,6-DIPHOSPHATE

The present invention provides a process for preserving the phosphorylating activity of brewer's yeast by means of the intracellular immobilization of the glycolytic enzymes by glutaraldehyde.

This allows to repeatedly use the same yeast in the phosphorylation of dextrose to fructose-1,6-diphosphate, besides laying the foundations for the continuous production thereof.

Fructose-1,6-diphosphate is known to be widely used in industry both as an intermediate in the glycolysis and because of the important part it plays in many metabolic processes, and of its wide application in the pharmaceutical field.

It is known a method for producing FDP based on the enzymatic phosphorylation of dextrose by inorganic phosphate.

Such known method consists in altering the permeability of the yeast cell walls by means of plasmolytic agents such as toluene, or detergents such as triton, or by the combined effect of temperature and the osmotic shock; thus the permeability of the cellular walls is increased, which allows FDP to flow out of the cytoplasm.

The FDP, prevented from taking part in the glycolysis cycle, accumulates in the suspension that contains the yeast cells.

An inconvenience of this process is however that the decreased capability of retention of the cell wall with respect to the cytoplasmatic material brings about as a consequence a leakage of the glycolytic enzymes, that disperse in the FDP-containing filtered or centrifuged solution.

Consequently, it is not possible to re-use yeast, as it is deprived of its enzymatic content as a result of each new phosphorylation; It is therefore impossible to carry out a continuous process.

To obviate the above inconvenience, the present invention provides a process for preserving the phosphorylating activity of yeast by means of the intracellular immobilization of the glycolytic enzymes by glutaraldehyde, so as to avoid such enzymatic leakage through the walls of permeabilized yeast cells. The phosphorylating capability of the yeast itself is thus preserved, making it possible the repeated employ thereof, as well as the development of a continual phosphorylating process of dextrose.

More specifically, the invention relates to a process for adjusting the permeability of the yeast cell wall, increasing it so as to allow the intracellular fructose-1,6-diphosphate to flow out, but blocking the glycolysis enzymatic complement inside the cell.

The process according to the invention provides first the permeabilization of the water-suspended yeast by means of the combined action of the temperature and the osmotic shock deriving from the addition of a concentrated solution of fructose and phosphates, and then the immobilization of the cytoplasmatic enzymes of the glycolysis inside the cell by means of their cross-linking with the intracellular proteins by effect of glutaraldehyde.

The invention will be better understood by the following detailed description, provided by mere way of non-limiting example.

The process consists substantially of the two following steps:

Step 1: a suspension of yeast cells is prepared by centrifuging a yeast culture of at least 4 days and re-suspending it in 50% w/v tap water. It should be noted that the same results were obtained by using the yeast surplus resulting from the beer production, yeast that may be obtained at a low cost.

The resulting suspension is heated to 35° C. and kept for 1 hour under slow stirring, after which there is added a concentrated solution of dextrose (2M) and phosphates (1M), at a volume ratio corresponding to 1/5 of the yeast suspension.

The permeability test is carried out 30–45 minutes after the addition of the mixture, and consists in treating a 1% cell solution in distilled water with a methylene blue (0.01%) and sodium acetate (2%) solution of the same volume: the cells that appear blue or light blue at microscopical examination are held to be made permeable.

In the case of yeasts that are refractory to such treatment (this may happen in particular when the yeast cultures are being renewed, usually in the winter season) a 1–5% plasmolytic agent can be added in the first heating step (satisfactory results were obtained with triton X-100 or toluene).

Step 2: to the permeabilized cell suspension obtained in the previous step may be added dithiothreitol (final 2 mM) to protect the enzymatic SH groups against oxidation, magnesium chloride (final 20 mM) and 10% v/v disintegrated yeast as additional protein supply, with a view to stopping the inhibiting action—if any—on the intracellular enzymes of glutaraldheyde, that should be added last, as binding agent at the final concentration amount of 0.25%.

The temperature of the yeast suspension is kept at 28° C. for the whole time, under slow stirring.

The disintegrated yeast is prepared by a common cell disintegrator of the glass ball homogenizer type, whereby at least 95% yeast cells is broken, using a 50% suspension (wet weight) of centrifuged yeast in a dextrose (1M) and potassium phosphate (0.6M) suspension, and operating at 4° C. in ice bath.

In order to reach the necessary degree of disintegration are necessary at least three successive cycles of 3' each, with 1 minute interval between one cycles and the next.

In this second step the glycolytic enzymes are kept inside the yeast cell.

Table 1 shows the effectiveness of the invention process, capable of avoiding the enzymatic leakage from the permeabilized yeast cells, and of allowing the repeated re-utilization thereof in phosphorylating dextrose to fructose-1,6-diphosphate.

TABLE 1

Distribution of the enzymatic activity over the first phosphorylation cycle.

| | (A) Exoquinase | | | |
|---|---|---|---|---|
| | Permeabilized Cells Control | | Permeabilized cells Cross-Linked according to the Invention | |
| | Residue | Supernatant | Residue | Supernatant |
| 1 hour | 92% | 8% | 94% | 5.5% |
| 7 hour | 47% | 45% | 82% | 5% |

TABLE 1-continued

Distribution of the enzymatic activity over the first phosphorylation cycle.

| 20 hour | 16% | 60% | 75% | 4.5% |
|---|---|---|---|---|

(B) Pyruvate Quinase

| | Immobilized Cells Controls | | Immobilized Cells Cross-Linked according to the Invention | |
|---|---|---|---|---|
| | Residue | Supernatant | Residue | Supernatant |
| 1 hour | 96% | 4% | 83% | 17% |
| 7 hour | 66% | 10% | 55% | 15% |
| 20 hour | 28% | 36% | 48% | 12% |

(the percentages refer to the total activity assessed at the beginning of phosphorylation).

The addition of dithiothreitol to the solution is meant to protect the enzymes fixed by glutaraldheyde from the SH groups oxidation.

Further studies carried out by the Applicant led to the findings that dithiothreitol, that is very expensive, can be replaced by a 10% v/v deproteinized and centrifuged disintegrated yeast, prepared as described above.

The present invention will be better understood by the following detailed examples.

EXAMPLE 1

60 g centrifuged fresh yeast, coming from the DREHER ale house of Popoli, (Saccharomyces carlsbergensis) are re-suspended in 40 ml tap water, with the addition of 2 ml of a 20% hexahydrate magnesium chloride solution, and of 20 ml nutrient mixture (2 m dextrose, 1M bibasic sodium phosphate and phosphoric acid q.s. to bring the PH to 6.5.). The suspension is heated in double boiler thermostat to 35° C. for 1 hour, under slow stirring to make the suspension homogeneous and the temperature uniform.

Then is added 60 ml disintegrated yeast, 30 mg dithiothreitol and, after cooling the whole mass to 28° C., 1 ml 25% glutaraldheyde solution, under constant stirring.

After 30' the yeast is ready to be used for a cycle of repeated phosphorylations.

EXAMPLE 2

60 g centrifuged fresh yeast, coming from the WHURER ale house of Battipaglia, cross-linked as described in the Example 1, is used over 10 consecutive phosphorylation cycles according to the following process.

To the glutaraldhyde-treated final suspension is added another 30 ml nutrient mixture. At the end of stirring the mixture is incubated at 28° C. for 8 hours, during which a production of considerable amount of $CO_2$ and froth occurs. After centrifugation the FDP-containing supernatant is separated from the yeast cells, that are re-suspended in tap water (final volume: 100 ml). Then are added 20% magnesium chloride (2 ml), centrifuged and deproteinized disintegrated yeast (10 ml) and nutrient mixture (50 ml). The whole is incubated at 28° C. without stirring for 10 hours, then the cells are again centrifuged, decanted and re-suspended; each cycle is repeated in this manner over a whole week. The development of $CO_2$ is always constant, which indicates that the cells remain active. In Table 2 are set out the comparative data of ten consecutive cycles carried out with glutaraldhyde-treated yeast and untreated control yeast, whereby is evidenced the protective action of the invention process on the phosphorylating activity.

TABLE 2

Phosphorylation yield in the repeated utilization of the same yeast.

| | g. PRODUCED FDP/ 60 g. DAMP YEAST RESIDUE | |
|---|---|---|
| PHOSPHORYLATION CYCLES | Control Yeast | Yeast treated according to the Invention |
| 1. | 5.1 | 5.8 |
| 2 | 6.3 | 6.6 |
| 3 | 5.7 | 7.3 |
| 4 | 3.5 | 7.2 |
| 5 | 2.7 | 6.9 |
| 6 | 2.1 | 7.1 |
| 7 | 0.9 | 6.6 |
| 8 | 0.7 | 6.0 |
| 9 | 0.6 | 5.9 |
| 10 | 0.3 | 4.9 |

We claim:

1. A process for preserving the phosphorylating activity of brewer's yeast applied to the production of fructose-1,6-diphosphate, wherein the following steps are provided:
    (a) permeabilizing the cell wall, in order to allow fructose-1,6-diphosphate to flow out from the cytoplasm, by adding 0.5 volume hypertonic solution to 1 volume of a yeast suspension of 60% w/v yeast in tap water, and heating for one hour to 35° C. under slow stirring;
    (b) preparing a disintegrated yeast extract suitable for use as a protecting agent against the oxidation of the SH groups of the glycolytic enzymes during the repeated phoshorylation cycles, by disintegrating a yeast suspension in a hypertonic solution of 1M glucose and 0.5M potassium phosphate by means of a glass ball homogenizer, incubating the disintegrated cell suspension for 2 h at 28° C., deproteinizing by heating at 100° C. for 10' and centrifuging 8000 revolutions for 30'; and
    (c) immobilizing the glycolytic enzymes inside the cell, by cross-linking with intracellular proteins, wherein glutaraldehyde is added to the suspension of the permeabilized yeast cells, and to which is added disintegrated yeast extract at a final concentration of glutaraldehyde of 0.25–1% w/v, at 28° C. under constant and slow stirring.

2. A process according to claim 1, wherein the yeast cells are of Saccharomyces carlsbergensis.

3. A process according to claim 1, wherein a 1–5% amount of a plasmolytic agent is added to the yeast suspension before the addition of the solution of glucose and phosphate.

4. A process according to claim 3, wherein the said plasmolytic agent is either an organic solvent or a detergent.

5. A process according to claim 1, wherein the yeast extract is added to the phosphorylation mixture in an amount of 5–15% v/v.

6. A process according to claim 1, wherein 10% (v/v) disintegrated yeast is added to the permeabilized yeast cells.

* * * * *